US005611784A

United States Patent [19]
Barresi et al.

[11] Patent Number: 5,611,784
[45] Date of Patent: Mar. 18, 1997

[54] MANUAL DISPENSING AID FOR A SYRINGE

[75] Inventors: Thomas Barresi, Reno, Nev.; Robert Scalese, Truckee, Calif.; Eric Riedi; Jon E. Frudden, both of Reno, Nev.; Randy Hall, Carson City, Nev.; Son Nguyen, Sparks, Nev.; Robert Anderson, Reno, Nev.

[73] Assignee: Hamilton Company, Reno, Nev.

[21] Appl. No.: 357,528

[22] Filed: Dec. 16, 1994

Related U.S. Application Data

[63] Continuation of Ser. No. 85,500, Jun. 30, 1993, abandoned.

[51] Int. Cl.⁶ .................................................. A61M 5/00
[52] U.S. Cl. ..................... 604/211; 604/224; 604/246; 604/67; 128/DIG. 1
[58] Field of Search ..................... 128/DIG. 1; 604/186, 604/187, 207–211, 224, 225, 227, 228, 246, 67

[56] References Cited

U.S. PATENT DOCUMENTS

| | | |
|---|---|---|
| 2,198,666 | 4/1940 | Gruskin . |
| 3,270,548 | 9/1966 | Marbach ............................. 604/207 |
| 3,613,952 | 10/1971 | Gilmont . |
| 3,749,284 | 7/1973 | Kloehn . |
| 3,799,406 | 3/1974 | St. John et al. . |
| 3,833,030 | 9/1974 | Waldbauer, Jr. et al. ............. 604/186 |
| 3,907,009 | 9/1975 | Dobbins ............................. 604/207 |
| 4,357,971 | 11/1982 | Friedman . |
| 4,470,317 | 9/1984 | Sabloewski et al. . |
| 4,527,437 | 7/1985 | Wells . |
| 4,567,780 | 2/1986 | Oppenlander et al. . |
| 4,627,835 | 12/1986 | Fenton, Jr. . |
| 4,671,123 | 6/1987 | Magnussen, Jr. . |
| 4,841,225 | 6/1989 | Meyer . |
| 4,882,536 | 11/1989 | Meyer . |
| 4,931,041 | 6/1990 | Faeser ................................ 604/155 |
| 4,959,056 | 9/1990 | Dombrowski et al. ............... 604/186 |
| 4,978,335 | 12/1990 | Arthur, III .......................... 604/67 |
| 4,988,337 | 1/1991 | Ito ..................................... 604/224 |
| 4,998,570 | 3/1991 | Strong ............................... 604/187 |

FOREIGN PATENT DOCUMENTS

1179888  2/1970  United Kingdom ................ 604/207

*Primary Examiner*—Corrine M. McDermott
*Assistant Examiner*—N. Kent Gring
*Attorney, Agent, or Firm*—Bernhard Kreten

[57] ABSTRACT

A releasably attachable manual dispensing aid is operable with a syringe having a syringe body and a syringe plunger that is movable within the syringe body. The dispensing aid includes a dispensing aid body that is releasably attachable to the syringe body. The dispensing aid further includes a dispensing aid plunger that is attachable to the syringe plunger, and has a slide that is slidable within the dispensing aid body. A fine adjustment, bottom stop, Chaney stop, and/or drag brake for the slide are optionally provided. An electronic linear position measuring device has a first portion fixed to the dispensing aid body and a second portion fixed to the dispensing aid plunger. Optionally, the dispensing aid includes a microprocessor that receives as inputs a calibration value for a particular syringe and the position signal, and determines as an output signal the true volume of liquid displaced by the syringe plunger movement.

41 Claims, 7 Drawing Sheets

MANUAL DISPENSING AID FOR A SYRINGE

This application is a continuation of application Ser. No. 08/085,500, filed Jun. 30, 1993 now abandoned.

This invention relates to apparatus for use with syringes, and, more particularly, to a manual controller for microsyringes.

A syringe is a familiar device having a hollow tubular syringe body and a syringe plunger that slides within the syringe body. A volume of liquid is drawn into the syringe body by the withdrawing of the syringe plunger. That volume is dispensed by moving the syringe plunger forward to displace the liquid. Most syringe bodies have graduations marked on the sides of the syringe bodies to assist the user in estimating the amount of liquid that is drawn into and ejected from the syringe.

A microsyringe is a device that permits the dispensing of accurate volumes of liquids. A microsyringe is similar in construction to a conventional medical syringe and has a microsyringe body and a microsyringe plunger. The microsyringe dispenses liquids more accurately than does the medical syringe due to control of the interior bore diameter of the syringe body, control of the relative geometry of the bore and the plunger, and care taken to prevent leakage around the plunger. Microsyringes are typically used in scientific applications such as the injection of relatively small, accurate volumes of liquids into chromatographs and other instruments.

One of the ongoing problems in using the microsyringe is determining and controlling the volume of liquid that is drawn into the microsyringe body. The amount of liquid must be more precisely determined than for most medical applications. Moreover, the microsyringe is sometimes used for mixing functions as part of its dispensing role. That is, a first precise volume, less than the total volume capacity of the microsyringe, of a first liquid may be drawn into the microsyringe. Without ejecting the first liquid, a second precise volume may be thereafter drawn into the microsyringe. Further precise amounts of other liquids may be drawn into the microsyringe, so that the various liquids mix together. Once the mixture is formed, it may be ejected into a single receiver or several different receivers in precise amounts.

At the present time, the user of the microsyringe is required to view the graduations on the side of the microsyringe body in order to estimate the amount of fluid drawn into or ejected from the syringe. The plunger must be moved precisely in accordance with those graduations. Errors can be made, particularly in poor lighting conditions, where multiple complex operations are required, or where the operator is fatigued.

A number of approaches have been advanced for improving upon this situation. For example, fully automated dispensing devices have been developed. These devices are complex and bulky, and not really suited to assist in manual dispensing of liquids with a syringe or microsyringe. Manual digital dispensers, such as that of U.S. Pat. No. 4,959,056, have also been proposed. In the device of the '056 patent, the syringe is inserted into the dispensing device. The plunger of the syringe is movable by a lead screw operable by a knob, and there is a digital display so that the operator can read the position of the syringe plunger. While advancing the art, this digital dispenser is still not fully satisfactory for many applications. It is bulky and requires an unfamiliar screwing motion rather than the familiar linear motion normally associated with the operation of a syringe. If the pitch of the lead screw is large so that dispensing can be accomplished quickly with few turns of the screw advance knob, accuracy of measurement is likely to be low. If the pitch of the lead screw is small to achieve accurate measurements, the dispensing procedure requires an unacceptably long period of time.

Thus, there remains a need for an improved dispensing aid for a syringe or microsyringe. Although the need has arisen primarily in relation to the microsyringe, it may also be experienced in many syringe applications, and hereinafter the term "syringe" will be used as including both medical syringes and microsyringes.

The present invention fulfills this need, and further provides related advantages.

SUMMARY OF THE INVENTION

The present invention provides a manual dispensing aid for a syringe that clips onto a syringe and can later be readily removed for subsequent use with another syringe. The dispensing aid is light in weight, is convenient to use, and has a linear movement that can be readily operated in its preferred uses. There is an accurate digital readout that permits the user to determine precisely the amount of fluid drawn into or ejected from the syringe. In one embodiment, a calibration feature enables the syringe user to improve the accuracy of the process even further by inputting a calibration factor for the syringe to correct for variations in the volume of the syringe within manufacturing tolerances.

In accordance with the invention, a releasably attachable manual dispensing aid is operable with a syringe having a syringe body and a syringe plunger slidable within the syringe body. The dispensing aid comprises a dispensing aid body and means for releasably attaching the dispensing aid body to the syringe body. There is further a dispensing aid plunger slidable within the dispensing aid body and means for releasably attaching the dispensing aid plunger to the syringe plunger. An electronic linear position measuring device has a first portion fixed to the dispensing aid body and a second portion fixed to the dispensing aid plunger.

In this basic form of the invention, the dispensing aid having a two-piece, linearly slidable construction clips onto the respective pieces of the two-piece, linearly slidable construction of the syringe. The position measuring device reads the position of the dispensing aid plunger and the dispensing aid body relative to each other, and provides this value as an output, preferably on a digital display visible to the operator and optionally to an output to another device such as a computer via a cable.

This dispensing aid is convenient to operate, because it allows the user of the syringe to draw and eject fluid with one hand, and with a linear motion that is familiar to syringe users. The user easily reads the linear position or volume measurement on the display. Once the dispensing operation is complete, the syringe is separated from the dispensing aid, so that the dispensing aid can be used with another syringe.

An emerging need in some areas of microsyringe applications is achieving highly accurate injection quantities. The required accuracy for some applications is so great that the manufacturing tolerances achieved in normal microsyringe manufacturing operations are not sufficient to achieve the required accuracy. Thus, for example, if the required volumetric accuracy of a microsyringe application is to within 0.1 microliter, a microsyringe manufactured to within 0.5 microliters nominal volumetric tolerance would be unacceptable. One solution is to improve the accuracy of the manufacturing operation, which may either be impossible or may be achieved only at very great manufacturing cost increases.

A further embodiment of the present invention provides an alternative approach to achieving improved volumetric dispensing accuracy of microsyringes, without changing the manufacturing tolerances. In accordance with this aspect of the invention, the dispensing aid comprises a dispensing aid body and means for releasably attaching the dispensing aid body to a syringe body. There is a dispensing aid plunger slidable within the dispensing aid body and means for releasably attaching the dispensing aid plunger to the syringe plunger. An electronic linear position measuring device produces an output linear position signal responsive to the relative position of the dispensing aid body and the dispensing aid plunger. A calibration value representative of the volumetric characteristics of a particular syringe is provided through an input terminal to a microprocessor which receives the output linear position signal of the linear position measuring device and the calibration value. The microprocessor produces a microprocessor output signal in which the linear position of the syringe plunger relative to the syringe body is corrected for the calibration value. There is a display for the microprocessor output signal.

This approach allows a volumetric calibration factor determined during the manufacture of the syringe to be input to the dispensing aid, thereby effectively customizing the dispensing aid to the particular syringe to which it is attached. Thus, rather than changing the manufacturing methodology of the syringe, the syringe is instead calibrated at the conclusion of the manufacturing operation. The calibration is readily accomplished by comparing the actual volume within the syringe body to the nominal value determined by the linear motion of the syringe plunger. The calibration value can be provided as a single number that can be interpolated for intermediate volume values, or in the case of the most extreme accuracy requirements as a lookup table or graphical calibration relation.

Whatever the form of the calibration, the calibration value is input to the dispensing aid when the dispensing aid is attached to the calibrated syringe. The input terminal can be manual in form, or can be an automatically reading terminal such as a microchip memory in the syringe body that is automatically read by the dispensing aid. The manual approach is suitable in the vast majority of cases, to keep the cost and size of the dispensing aid low.

This aspect of the present invention therefore provides a direct link between the manufacturing process of the syringe and its use, in order to attain high accuracies when required. Instead of changing the manufacturing techniques at substantially increased costs, each syringe is custom calibrated and that calibration is provided to the dispensing aid. The graduations on the side of the syringe therefore become largely obsolete, for such high-accuracy applications.

The present invention thus provides a dispensing aid that in a basic form significantly increases the convenience of manually using the conventional syringe for many applications. In a more advanced form, the dispensing aid having a calibration-utilizing function improves the accuracy of dispensing operations with little increase in manufacturing cost of the syringe.

Other features and advantages of the present invention will be apparent from the following more detailed description of the preferred embodiment, taken in conjunction with the accompanying drawings, which illustrate, by way of example, the principles of the invention.

BRIEF DESCRIPTION OF THE DRAWINGS

FIG. 7 presents two views of a Chaney stop mechanism, where

DETAILED DESCRIPTION OF THE INVENTION

Figure 1:
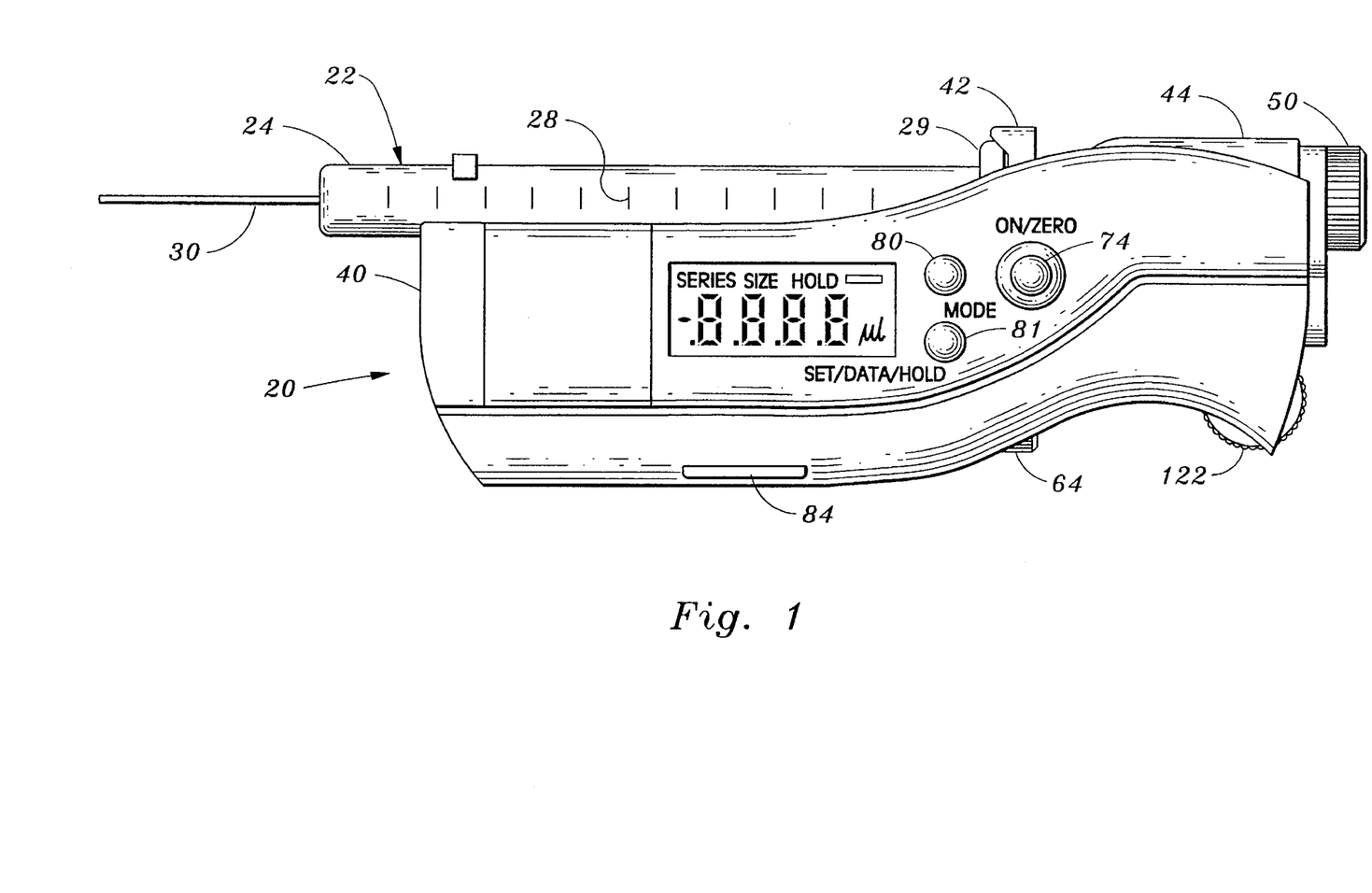
FIG. 1 is an elevational view of a first side of a dispensing aid and a syringe clipped thereto.
Figure 2:
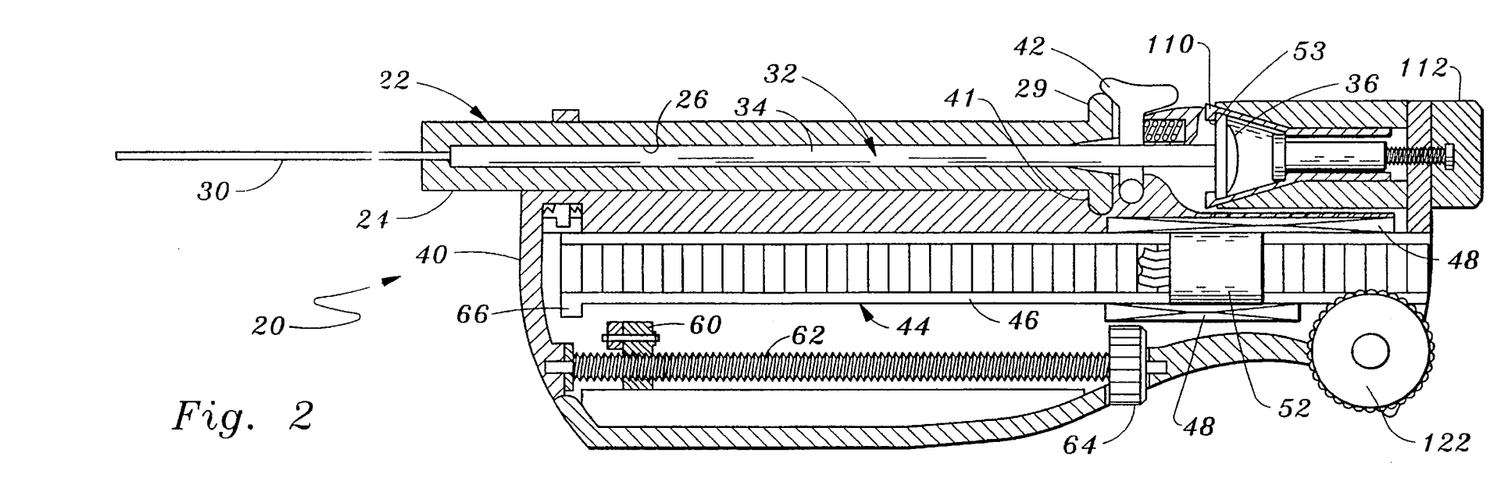
FIG. 2 is a sectional view of the dispensing aid and syringe of FIG. 1.

FIGS. 1 and 2 depict a manual dispensing aid 20 used in conjunction with a syringe 22. The syringe 22 is of a generally conventional form, and, by way of example and not limitation, includes microsyringes for analytical use, medical syringes, and other syringes. The syringe 22 has a syringe body 24 with an internal bore 26. The syringe body 24 is typically made of glass or plastic and optionally has graduations 28 marked on its side. There is preferably a slight radial enlargement 29 at one end of the syringe body 24.

Optionally, a needle 30 or other type of injection connector is provided in communication with the bore 26 of the syringe body 24 at the end opposite the enlargement 29. Extending through the bore 26 along a long plunger axis is a plunger 32 comprising a plunger rod 34 made of metal such as a nickel alloy. At the end of the plunger 32 remote from the needle 30, a plunger button 36 is attached to the plunger rod 34. Liquid is drawn into the syringe body 24 by withdrawing the plunger rod 34 (toward the right in FIG. 1), and liquid is ejected from the syringe body 24 by depressing the plunger rod 34 (toward the left in FIG. 1).

Syringes operable with the present invention are well known in the art and are available commercially, such as, for example, the Series 700 syringes available from Hamilton Company, Reno, Nev.

The dispensing aid 20 includes a dispensing aid body 40 which forms a housing sized to receive the syringe 22 therein. A releasable attachment, preferably in the form of a recess 41 formed in the dispensing aid body 40 to receive the enlargement 29 and a cooperating clip 42, is sized and positioned to permit the releasable attachment of the syringe body 24 to the dispensing aid body 40. The dispensing aid 20 further includes a dispensing aid plunger 44 having a slide 46 disposed to slide linearly along a long axis within a bearing set 48 in the dispensing aid body 40.

Figure 3:
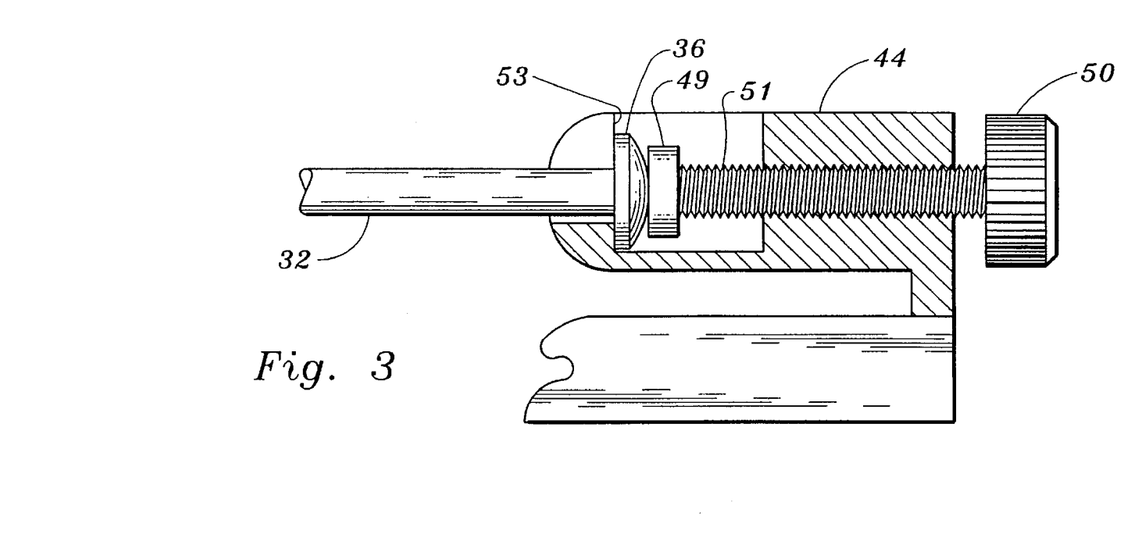
FIG. 3 is an enlarged sectional view of a detail of a dispensing aid and syringe, similar to that of a portion of FIG. 2, showing an alternative embodiment for locking the syringe plunger to the dispensing aid plunger.

A releasable attachment, such as a collet 110 driven by a clamp screw 112 captures the plunger button 36 therein. The turning of the clamp screw 112 retains the plunger button 36 against the interior of a recess 53 in the dispensing aid plunger 44, to permit the releasable attachment of the syringe plunger 32 to the dispensing aid plunger 44. FIG. 3 depicts an alternative arrangement. Here, a block 49 driven by a locking knob 50 through a screw 51 retains the plunger button 36 in the recess 53.

The dispensing aid 20 is thus cooperatively configured with the syringe 22. The configuration permits the syringe body 24 to be releasably attached to the dispensing aid body 40 and the syringe plunger 32 to be releasably attached to the dispensing aid plunger 44. In the illustrated preferred approach, the syringe body 24 snaps into the recess 41 to be locked by the clip 42. The plunger button 36 slips into the recess 53 and is locked into place by rotating the clamp screw 112, or with the locking block arrangement of FIG. 3. In operation, the sliding action of the dispensing aid 20 is substantially the same as that of the syringe 22, so that the syringe plunger 32 can be operated in its intended fashion by moving the dispensing aid plunger 44 linearly relative to the dispensing aid body 40. This movement in turn moves the syringe plunger 32 relative to the syringe body 24.

An electronic linear position measuring device 52 is provided to sense the position of the dispensing aid plunger 44 relative to the dispensing aid body 40, and thence provide the position of the syringe plunger 32 relative to the syringe body 24. As shown schematically in FIGS. 8 and 9, the position measuring device 52 has a first portion 54 fixed to the dispensing aid body 40 and a second portion 56 fixed to the dispensing aid plunger 44. The first portion and the second portion include metallic plates. The capacitance between the plates is a measure of the degree to which the plates are in full facing contact. As the first portion 54 and the second portion 56 are moved relative to each other, due to the relative movement of the dispensing aid body 40 and the dispensing aid plunger 44, the degree of facing contact is changed and the capacitance of the circuit is changed. Thus, the second portion 56 provides a first position indicator and the first portion 54 provides a second position indicator. One of the portions 54, 56 can be considered a position sensor while the circuit on the other portion 54, 56 can be considered to provide indicia of the position of the two portions 54, 56 relative to each other. The analytical approach is depicted in more detail in FIGS. 8 and 9 and discussed subsequently. Capacitance linear position measuring devices operable in the present invention are described in U.S. Pat. Nos. 4,841,225 and 4,882,535, whose disclosures are incorporated by reference, and are available commercially.

Figure 4:
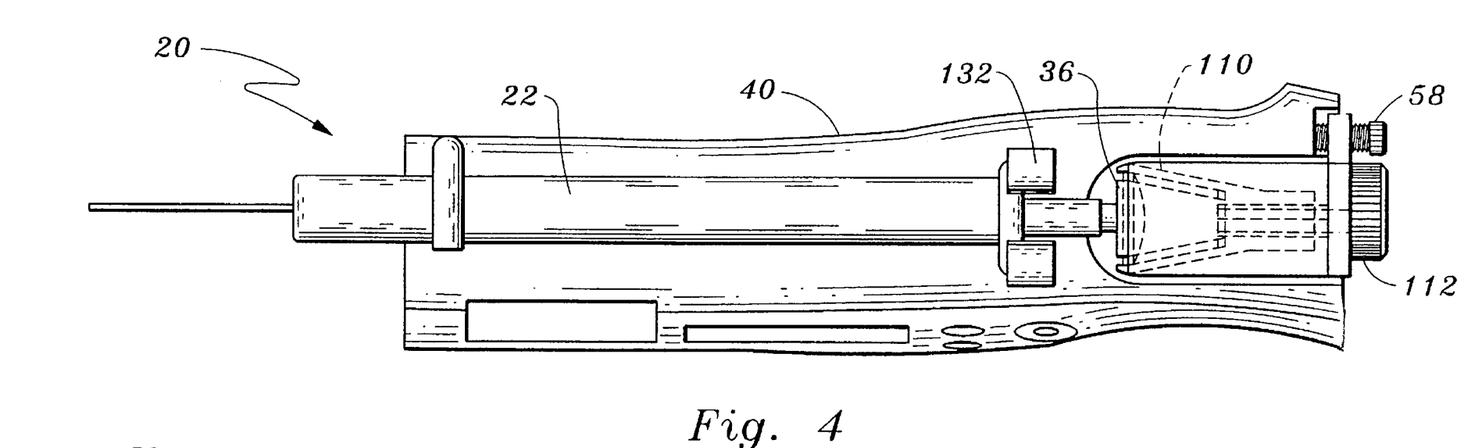
FIG. 4 is a plan view of the dispensing aid and syringe of FIG. 1, with portions broken away to show internal structure.

Optionally but desirably, stops for the relative movement of the dispensing aid body 40 and the dispensing aid plunger 44 are provided. A first stop 58, also termed a bottoming stop and shown in FIGS. 4 and 5, limits the extent to which the dispensing aid plunger 44 can be inserted into the dispensing aid body 40. The first stop 58 is here depicted (FIG. 4) to be a screw-adjustable stop.

A second stop 60 limits the extent to which the dispensing aid plunger 44 can be withdrawn from the dispensing aid body 40 during filling. The second stop 60 is here depicted (FIG. 2) as driven by a screw 62 that is set by an externally accessible stop-set wheel 64. At its set position, the second stop 60 blocks the movement of the slide 46 by engaging a projection 66 of the slide, so that the dispensing aid plunger 44 cannot be withdrawn past the preselected position. In its preferred form, the second stop 60 is integrated with a "Chaney stop" feature to be discussed subsequently. The second stop 60 can also be provided without incorporation of the Chaney stop structure.

Figure 5:
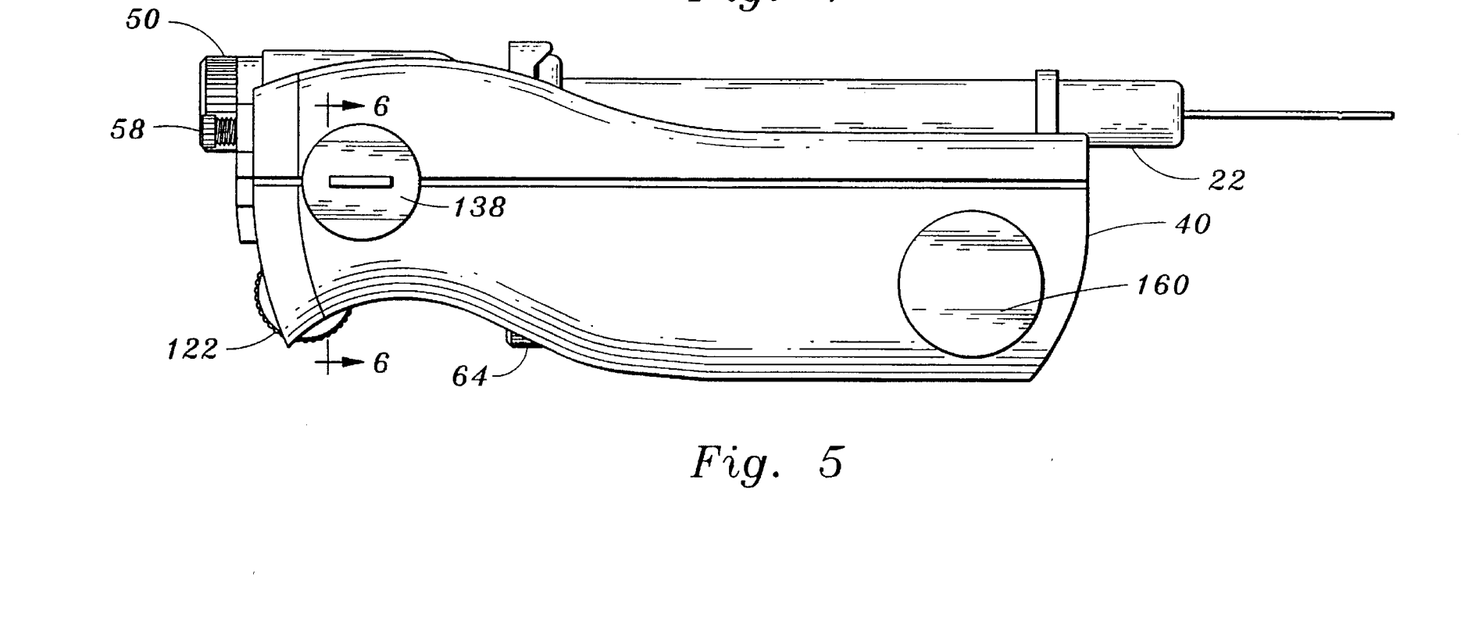
FIG. 5 is an elevational view of a second side of the dispensing aid and syringe of FIG. 1.
Figure 6:
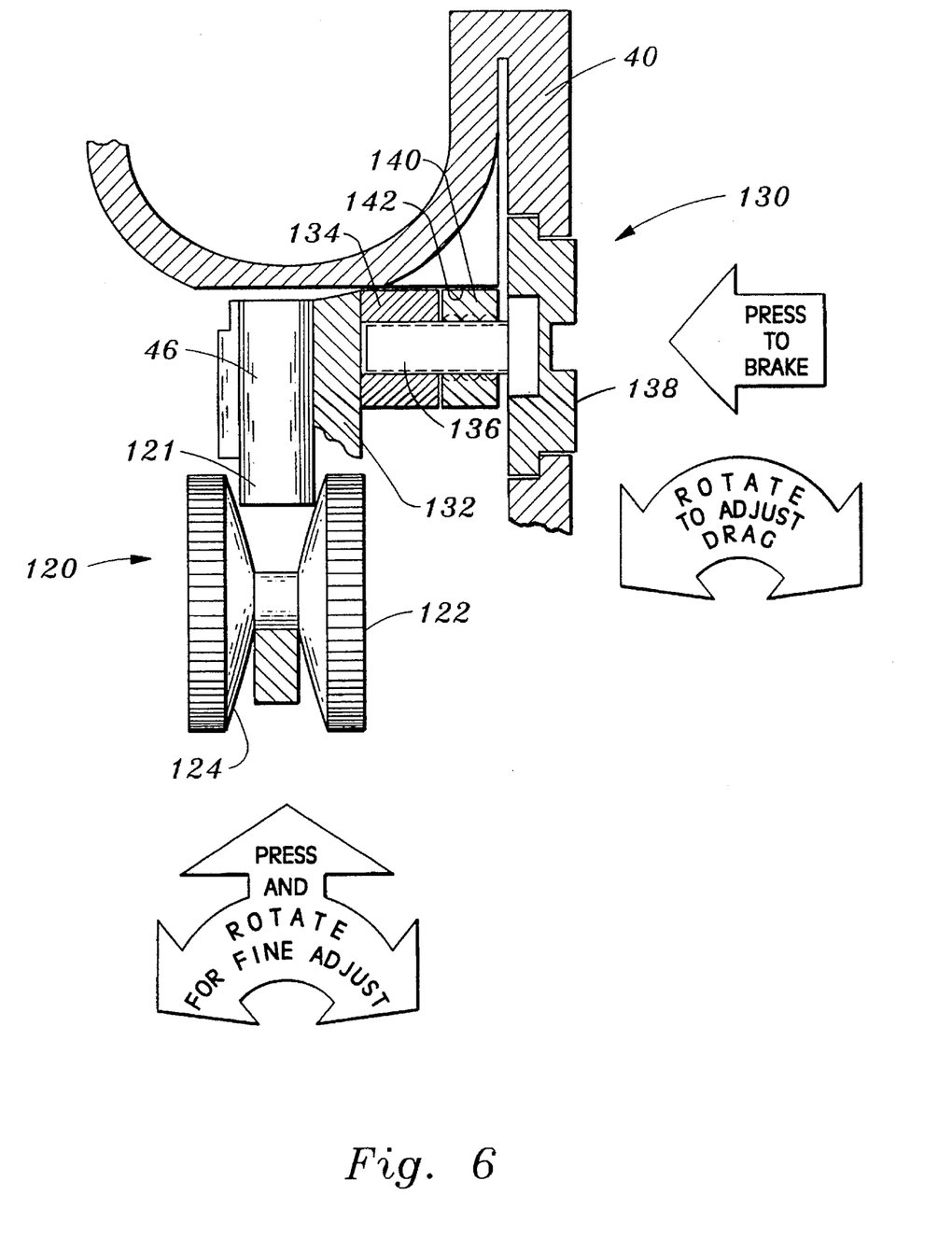
FIG. 6 is a sectional view taken along line 6—6 of the dispensing aid and syringe of FIG. 5, showing the fine adjust and brake mechanisms.

A fine adjust mechanism 120 for the dispensing aid 20 is preferably provided, as shown in FIG. 6. At its rearmost end, the slide 46 preferably has a rectangular shape with a lower end 121. A fine adjust thumbwheel 122, rotatably in supported the dispensing aid body 40, is externally accessible to the user, as seen in FIGS. 1, 2, and 5. The thumbwheel 122 has a tapered interior portion 124 that releasably engages the lower end 121 of the rectangular slide 46. The coarse position of the slide 46, and thence the syringe plunger 32, is determined by moving the dispensing aid plunger 44. For fine adjustments to the position so obtained, the thumbwheel 122 is pressed against the lower end 121 of the slide 46 by thumb pressure and the thumbwheel 122 is rotated by thumb motion to move the slide 46 and the syringe plunger 32 by a small amount.

FIG. 6 also depicts an adjustable drag brake mechanism 130 that is preferably provided. It is observed that, particularly in making fine adjustments of the syringe, it may be helpful to apply a drag force to increase friction forces on the slide. The mechanism 130 permits an adjustable braking force to be applied to the slide during use of the dispensing aid 20. The drag brake mechanism 130 includes a brake pad 132 that is compliantly mounted to the dispensing aid body 40, and contacts a portion of the slide 46. The brake pad 132 is contacted by an actuating spring 134 made of an elastomeric material, which in turn is activated through an actuating arm 136 by pushing an externally accessible (FIG. 5) drag brake adjust button 138. Pushing the button 138 forces the actuating spring 134 against the brake pad 132. This movement in turn forces the brake pad 132 against the slide 46 to apply a drag force against the movement of the slide 46 and thence the syringe plunger 32.

The drag force applied by the drag brake mechanism 130 is adjustable. The actuating arm 136 is externally threaded along a portion of its length, and has threaded thereto a floating nut 140. The floating nut 140 is square in section in the preferred design, and resides in a square recess 142 in the dispensing aid body 40. The floating nut 140 can by moved inwardly and outwardly by the turning of the actuating arm 136 by the drag brake adjustment button 138, but cannot rotate around the axis of the actuating arm 136. An inward movement of the floating nut 140 causes it to press against the elastomeric actuating spring 134 and force it against the brake pad 132. The spring force of the actuating spring 134 thereby modifies the force that is transmitted to the break pad 132 and thence is applied as a drag force to the slide 46.

The basic second stop mechanism for operating the second stop 60 has been previously discussed. The second stop mechanism may be provided in the manner shown in FIG. 2, or it may be utilized as part of a Chaney stop mechanism. A Chaney stop mechanism is a known approach for use in accurate dispensing from a syringe. In the present case, however, it has been adapted for use with the dispensing aid 20 of the invention.

Figure 7A:
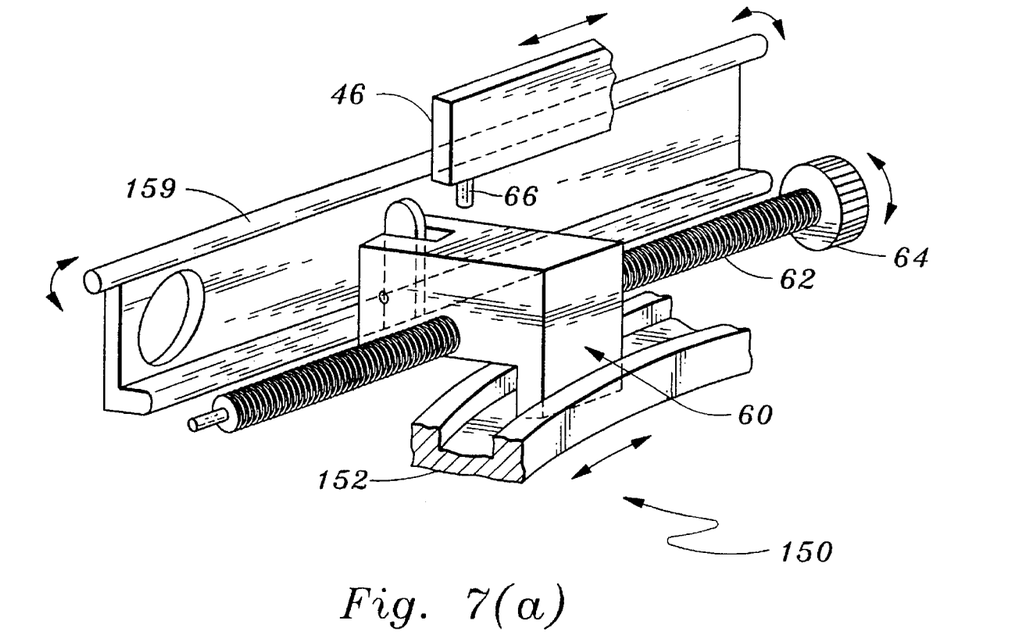
FIG. 7(a) is a perspective view and FIG. 7(b) is an end view.

The Chaney stop mechanism is shown in greater detail in FIG. 7. In the presently preferred approach as shown in FIG. 7(a) (absent a portion of the mechanism for clarity), a Chaney stop mechanism 150 includes the screw shaft 62, operated by the stop set wheel 64, that extends parallel to the syringe body 24 within the dispensing aid body 40 adjacent to the slide 46. The second stop 60 rides in an axial channel 156 extending parallel to the syringe body in the interior of the dispensing aid body 40. In the Chaney stop mechanism 150, the second stop 60 does not engage the projection 66 unless the Chaney stop mechanism is activated.

Figure 7B:
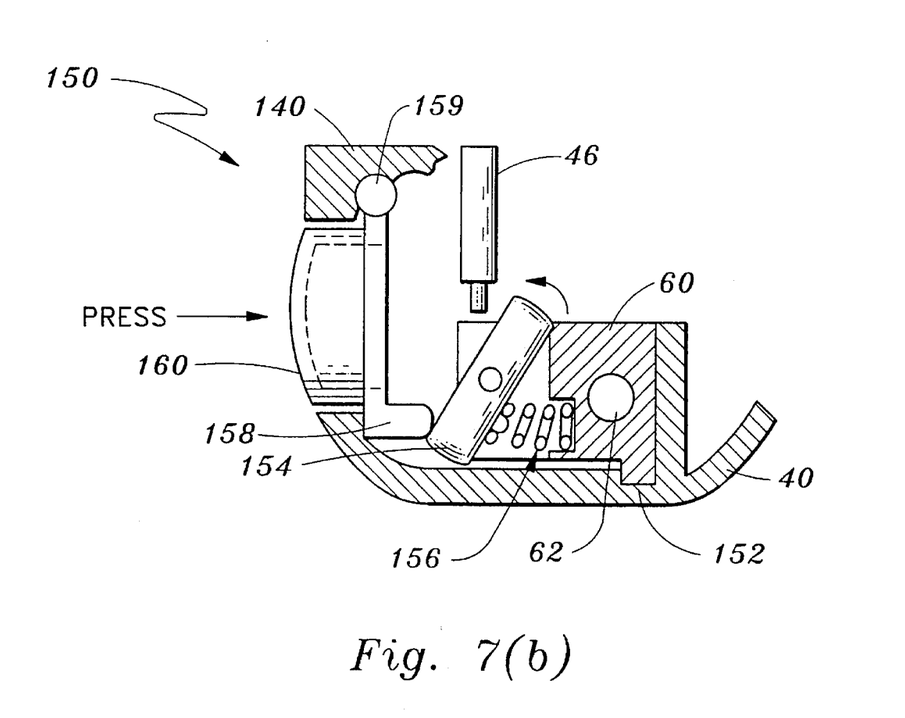

To cause the second stop 60 to engage the projection 66 on the slide 46, a stop blade 154 is pivotably mounted to the second stop 60, as shown in FIG. 7(b). The stop blade 154 is biased by a spring 156 to a first position whereat the stop blade 154 cannot contact the projection 66 on the slide 46. The stop blade 154 is rotatable to second position whereat the stop blade 154 is contactable to the projection 66 by pressing an externally accessible brake button 160 (see also FIG. 5). A rocker arm 158 is pivotably mounted to the dispensing aid body 40 by a rocker pivot 159. The depression of the brake button 150 presses against the rocker arm 158, causing it to rotate to press against the stop blade 154. The stop blade 154 thereby rotates against the force of the spring 156 so that the stop blade 154 is at the second position to engage the projection 66. Release of the brake button 160 permits the stop blade 154 to rotate back to the first position so that the projection 66 cannot be engaged.

The Chaney stop mechanism 150, where provided, is typically utilized in a sequence of an overfill, stop, and inject operation. To utilize the Chaney stop mechanism in this manner, the brake button 160 is released to deactivate the stop. The slide 46 is drawn back to overfill the syringe 22. The brake button 160 is pressed to activate the Chaney stop and the slide 46 is pressed to pre-dispense liquid from the syringe 22 until the projection 66 contacts the stop blade 154. At this point, the syringe 22 contains a preselected amount of fluid. This fluid is dispensed by releasing the brake button 160 and pressing the slide 46.

Figure 8:
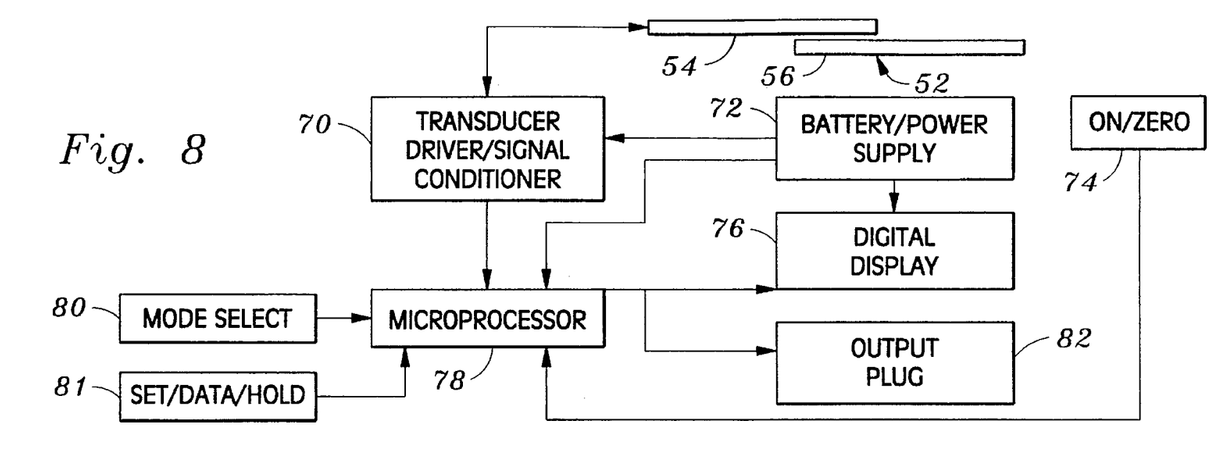
FIG. 8 is an electrical schematic diagram of the dispensing aid of FIG. 1.

FIG. 8 is a schematic diagram for the electronics of the present invention. The position measuring device 52 is part of a capacitance measuring circuit driven by a transducer driver/signal conditioner 70. The transducer driver/signal conditioner 70 applies a voltage across the first portion 54 and the second portion 56. Power is required for this circuit, and a battery/power supply 72 is provided. One important feature of the present invention is that this transducer driver/signal conditioner 70 and other power-consuming components of the dispensing aid 20 require very little power. The battery/power supply 72 may therefore be a conventional coin-shaped lithium battery such as that used in a watch.

The transducer driver/signal conditioner 70 also measures the capacitance of the circuit including the position measuring device 52. It supplies that measurement to a digital display 76 as an indication of the extent of linear movement between the first portion and the second portion.

In the presently preferred case, the output of the transducer driver/signal conditioner 70 is provided to the digital display 76 indirectly. That output signal is first provided to a microprocessor 78 activated by a user-accessible "on" switch 74. (In the preferred embodiment there is no "off" switch. The microprocessor 78 discontinues operation after a preselected period of time, such as 5 minutes, if no activity occurs in that time period.)

There is further a user-accessible mode select input button 80. The user selects a mode of operation for the microprocessor 78 through the button 80 and permits the user to access the set-up sequence for the dispensing aid 20. The microprocessor 78 may send an output to the digital display according to the selected mode. set/data/hold control 81 is a multifunctional switch that permits the user to select a syringe type, series, size, or calibration ("set"), send data to an external computer ("data"), and maintain the display value ("hold") to permit the user to record the display value. In the "data" mode, the microprocessor 78 transmits a data string to an output plug 82, such as an RS-232 connector for transmission to an external device (not shown) such as a piece of instrumentation or a computer.

Figure 9:
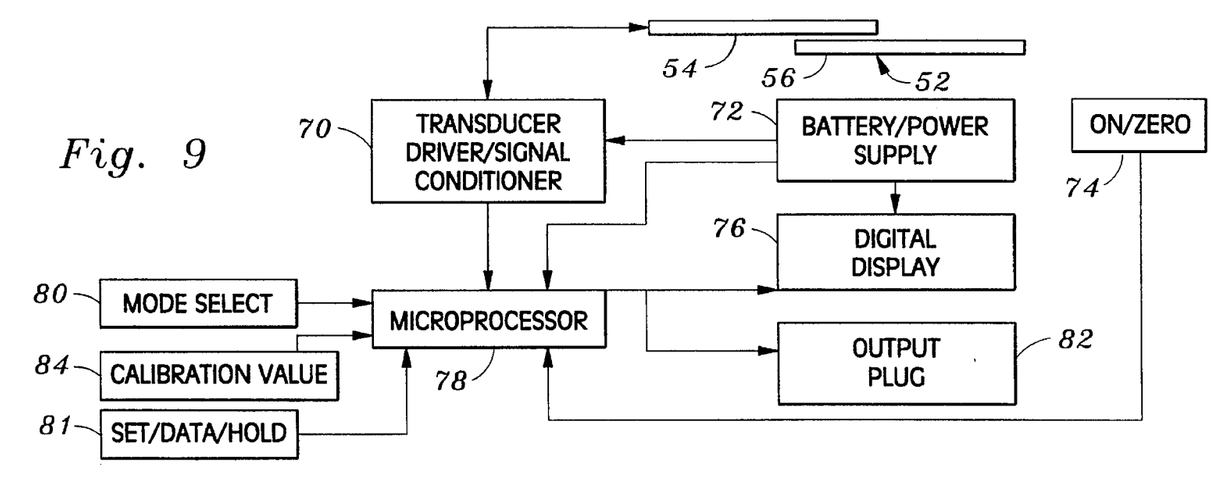
FIG. 9 is an electrical schematic diagram of a second embodiment of the dispensing aid of FIG. 1.

FIG. 9 illustrates a modified version of the electronics of the invention, which is used with the same physical structure as shown in FIGS. 1–2. In the embodiment of FIG. 9, the electronic circuitry of FIG. 8 is supplemented by the addition of a calibration value input 84 to the microprocessor 78. The calibration value expresses the relation between the actual volume contained within the interior of the bore 26 of the syringe 22, and some nominal value such as the linear position of the plunger rod 34. As an example, an idealized syringe may be designed to hold 100 microliters of liquid when the plunger rod 34 is withdrawn to the "100" graduation 28. However, due to manufacturing tolerances an actual syringe manufactured according to this design may actually hold 100.5 microliters of liquid. The calibration value expresses the relation between the actual and the idealized volumes, in this case 100.5/100. While this calibration value is near unity, in some applications the difference between the actual and the idealized volumes may be important. In performing a calibration, $$V = L/S \times C$$

where V is the calculated volume, L is the actual linear position of the syringe plunger, S is the scale length of the syringe on the same scale as L, and C is the syringe capacity.

The calibration value input 84 allows the calibration value to be provided to the microprocessor 78. In the microprocessor, the calibration value factor is applied to the linear position measurement from the position measuring device 52, to determine the true value of liquid. This true value is then output to the digital display as a volume value, not a linear position value. Thus, for example, continuing the above example, if the linear displacement value during dispensing is 50 and the calibration value is 100.5/100, the actual volume dispensed is (100.5/100)×50 or 50.25 microliters.

The ability to use the measured linear displacement to obtain a correct volume value has important consequences for some users. The dispensing aid can be customized for each individual syringe, if a high degree of accuracy is required that is greater than possible with normal manufacturing tolerances. On the other hand, if conventional accuracy within normal manufacturing tolerances is sufficient, a calibration value of 1.0 can be used. The calibration value is usually quite close to unity, and for many user applications no consideration of the calibration factor is necessary. Nevertheless, where high precision is required, this calibration approach allows the dispensing aid to be used with a single syringe, or with a succession of syringes, to attain a customized and calibrated volume output measurement. When the calibration approach is utilized, the graduations 28 marked on the syringe body 24 are not helpful to the syringe user, except to obtain a rough estimate of plunger position.

This approach also permits improved accuracy to be attained without changing the basic manufacturing approach A calibration step is required for each syringe, but this step can be readily accomplished at the end of the manufacturing process without modification to the underlying manufacturing technology of the syringe.

Figure 10:
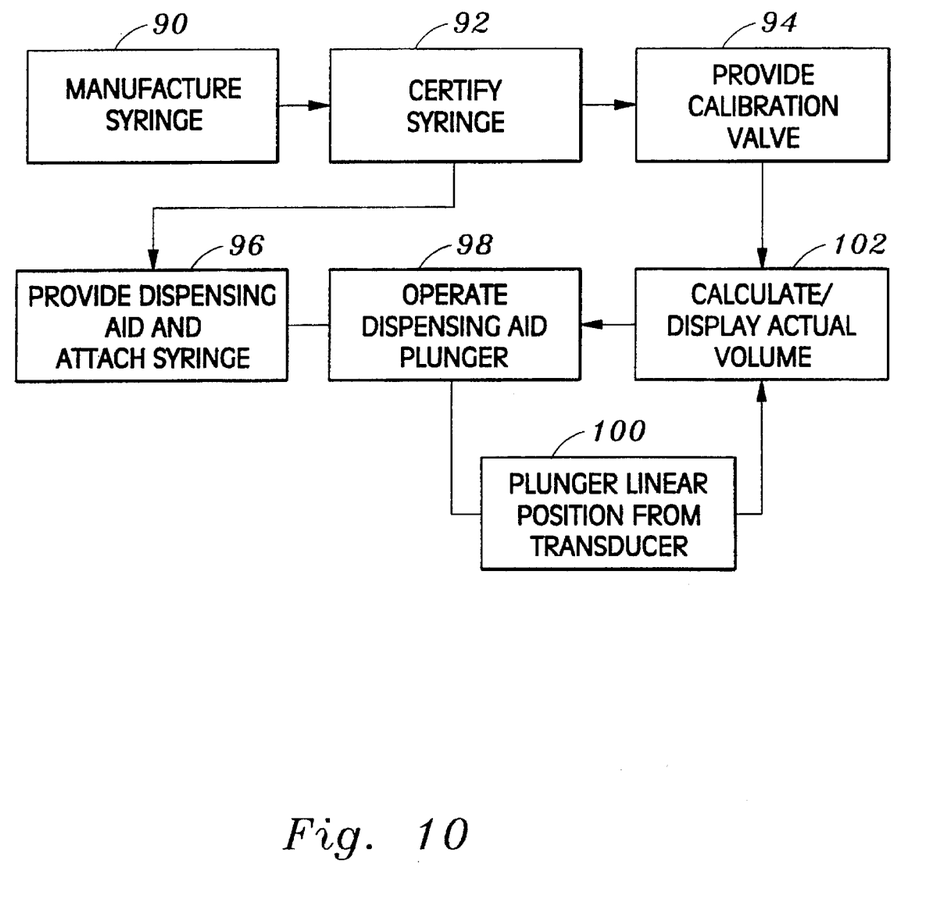
FIG. 10 is a process flow diagram for a method of dispensing liquids using the second embodiment of the dispensing aid.

FIG. 10 depicts the methodology for using the calibration approach in conjunction with the dispensing aid of the invention. The syringe is manufactured according to the normal approach, numeral 90. The syringe is certified or volumetrically measured in an appropriate manner, numeral 92. In the preferred approach, a volume of fluid is drawn into the syringe, by linearly displacing the plunger by a selected amount. The volume of fluid is thereafter measured. The ratio between the measured volume of fluid and the selected linear displacement is the calibration value. Graduations can be provided on the side of the syringe body if necessary, but these gradations are not used if the subsequent dispensing is accomplished by the dispensing aid of the invention. (In some instances it may be preferable not to provide graduations on the side of the syringe, so that the user does not inadvertently rely upon these graduations instead of the digital display.) This described approach for a single linear calibration value can be extended to a matrix of values corresponding to the full range of linear displacements. In most cases, however, a single linear calibration is sufficient.

The calibration value is associated with a particular syringe and is provided to the microprocessor 78 through the input 84, numeral 94 of FIG. 10. Various input techniques can be used. For example, in one approach the calibration value is stamped on the side of the syringe package and the user manually inputs the value to the microprocessor. In another approach, the calibration value is provided in a microelectronic or printed memory that is supplied with the syringe or affixed to the syringe and read by a reader in the calibration value input 84. For example, the calibration information may be placed into a bar code printed onto the side of the syringe and scanned into the microprocessor 78 through the input 84. This approach minimizes the possibility of human error in inputting a calibration value.

The dispensing aid 20 made according to the present approach and with the electronics of FIG. 9 is provided, numeral 96. The calibrated syringe is attached to the dispensing aid in the manner discussed previously, and the calibration value is provided to the microprocessor.

The dispensing aid is operated to draw liquid into the syringe by moving the dispensing aid plunger 44, numeral 98. The linear displacement of the plunger 44 is measured by the positioning measuring device 52, numeral 100. (The graduation markings on the syringe body are not used, because they are not strictly precise in this high-precision application.) The linear displacement is provided to the microprocessor 78. The calibration-corrected value of volumes is calculated according to the approach described previously, or any other operable calibration calculation, and displayed to the user of the syringe, numeral 102. Thus, the user views a calibration-corrected volume value, not a linear displacement value.

The present invention provides an important advance in the art. Without the calibration feature, accurate manual dispensing in a familiar manner can be readily accomplished. When calibration is added, the calibration-corrected volume is read directly by the user, so that highly accurate dispensing is possible. Although a particular embodiment of the invention has been described in detail for purposes of illustration, various modifications may be made without departing from the spirit and scope of the invention. Accordingly, the invention is not to be limited except as by the appended claims.

What is claimed is:

1. A releasably attachable manual dispensing aid operable with a syringe having a syringe body and a syringe plunger slidable within the syringe body, the dispensing aid comprising:

a dispensing aid body;

a slide that is slidable within the dispensing aid body;

means for releasably attaching the dispensing aid body directly to the syringe body;

a dispensing aid plunger connected to the slide, the dispensing aid plunger being directly graspable and operable by a human hand to produce a linear motion of the slide;

means for releasably attaching the dispensing aid plunger to the syringe plunger;

an electronic linear position measuring device having a first portion fixed to the dispensing aid body and a second portion fixed to the dispensing aid plunger;

a microprocessor which receives an output signal from the linear position measuring device;

a digital volume readout which receives an output signal from the microprocessor; and means for providing a volume calibration factor to the microprocessor.

2. A releasably attachable manual dispensing aid operable with a syringe having a syringe body and a syringe plunger slidable within the syringe body, the dispensing aid comprising:

a dispensing aid body;

a slide that is slidable within the dispensing aid body;

means for releasably attaching the dispensing aid body directly to the syringe body;

a dispensing aid plunger connected to the slide, the dispensing aid plunger being directly graspable and operable by a human hand to produce a linear motion of the slide;

means for releasably attaching the dispensing aid plunger to the syringe plunger;

an electronic linear position measuring device having a first portion fixed to the dispensing aid body and a second portion fixed to the dispensing aid plunger; and a fine adjustment wheel that engagably contacts the slide.

3. A releasably attachable manual dispensing aid operable with a syringe having a syringe body and a syringe plunger slidable within the syringe body, the dispensing aid comprising:

a dispensing aid body;

a slide that is slidable within the dispensing aid body;

means for releasably attaching the dispensing aid body directly to the syringe body;

a dispensing aid plunger connected to the slide, the dispensing aid plunger being directly graspable and operable by a human hand to produce a linear motion of the slide;

means for releasably attaching the dispensing aid plunger to the syringe plunger;

an electronic linear position measuring device having a first portion fixed to the dispensing aid body and a second portion fixed to the dispensing aid plunger;

a drag brake pad selectively engagable with the slide to apply a drag braking force to the movement of the slide;

an actuating arm attached to the drag brake pad;

a drag brake adjustment control operable on the actuating arm to apply the drag braking force to the drag brake pad;

a spring reacting between the dispensing aid body and the actuating arm; and means for adjusting a preload of the spring.

4. A releasably attachable manual dispensing aid operable with a syringe having a syringe body and a syringe plunger slidable within the syringe body, the dispensing aid comprising:

a dispensing aid body;

a slide that is slidable within the dispensing aid body;

means for releasably attaching the dispensing aid body directly to the syringe body;

a dispensing aid plunger connected to the slide, the dispensing aid plunger being directly graspable and operable by a human hand to produce a linear motion of the slide;

means for releasably attaching the dispensing aid plunger to the syringe plunger;

an electronic linear position measuring device having a first portion fixed to the dispensing aid body and a second portion fixed to the dispensing aid plunger;

a stop selectively engagable with the dispensing aid slide, the stop including;

a screw shaft extending parallel to the slide and having external threads thereon;

a block having internal threads thereon engaged to the external threads of the screw shaft;

a set wheel engaged to the screw shaft such that turning of the set wheel causes the threaded block to traverse in a direction parallel to the screw shaft;

means for selectively engaging the shaft, the means for engaging the shaft being mounted on the block; and means for activating the means for selectively engaging the shaft.

5. A releasably attachable manual dispensing aid operable with a syringe having a syringe body and a syringe plunger slidable within the syringe body, the dispensing aid comprising:

a dispensing aid body;

a slide that is slidable within the dispensing aid body;

means for releasably attaching the dispensing aid body directly to the syringe body;

a dispensing aid plunger directly graspable and operable by a human hand to produce a linear motion of the slide;

means for releasably attaching the dispensing aid plunger to the syringe plunger;

an electronic linear position measuring device comprising a first portion fixed to the dispensing aid body and having a first metallic electrode, a second portion fixed to the dispensing aid plunger and having a second metallic electrode disposed in a facing relation to the first metallic electrode, and means for measuring a capacitance of a circuit including the first metallic electrode and the second metallic electrode and producing an output linear position signal responsive to the measured capacitance;

a microprocessor which receives the output linear position signal of the means for measuring and produces a microprocessor output signal;

a readout which receives the microprocessor output signal; and means for providing a volume calibration factor to the microprocessor.

6. A releasably attachable manual dispensing aid operable with a syringe having a syringe body and a syringe plunger slidable within the syringe body, the dispensing aid comprising:

a dispensing aid body;

means for releasably attaching the dispensing aid body to the syringe body;

a dispensing aid plunger slidable within the dispensing aid body;

means for releasably attaching the dispensing aid plunger to the syringe plunger;

an electronic linear position measuring device that produces an output linear position signal responsive to the relative position of the dispensing aid body and the dispensing aid plunger;

an input terminal operable to receive a calibration value representative of the characteristics of a particular syringe;

a microprocessor which receives the output linear position signal from the linear position measuring device and the calibration value from the input terminal, and produces a microprocessor output signal in which the linear position of the syringe plunger relative to the syringe body is corrected for the calibration value; and a display of the microprocessor output signal.

7. The dispensing aid of claim 6 wherein the microprocessor includes means for determining a volume of liquid displaced by the syringe during movement of the syringe plunger, from the output linear position signal of the linear position measuring device and the calibration value, and for providing that volume value as the microprocessor output signal.

8. A method for dispensing liquids from a syringe, comprising the steps of:

manufacturing a syringe to a nominal volume standard;

determining a calibration value for an actual syringe volume as compared with the nominal volume standard of the step of manufacturing;

providing a dispensing aid having a volume readout signal and means for utilizing the calibration factor to determine the volume readout signal;

providing the calibration value to the dispensing aid; and manually dispensing liquid from the syringe using the dispensing aid; and the dispensing aid producing the volume readout signal concurrently with the step of manually dispensing, the means for utilizing of the dispensing aid correcting the volume readout signal for the calibration value.

9. The method of claim 8 wherein the step of providing a dispensing aid includes the step of providing:

a dispensing aid body;

means for releasably attaching the dispensing aid body to the syringe body;

a dispensing aid plunger slidable within the dispensing aid body means for releasably attaching the dispensing aid plunger to a syringe plunger;

an electronic linear position measuring device that produces an output linear position signal responsive to the relative position of the dispensing aid body and the dispensing aid plunger;

a microprocessor which receives the output linear position signal of the linear position measuring device and the calibration value, and produces a microprocessor output signal to the volume readout signal.

10. A precision volumetric liquid measuring and dispensing system for dispensing liquids from a syringe, the syringe including a body with a bore therein and a plunger linearly displaceable along a plunger axis into and out of the bore, the system comprising in combination:

a housing, means to secure the body of the syringe to said housing, a slide, means to secure said slide to said plunger with a long axis of said slide parallel to said plunger axis and adjacent said housing, said slide including indicia spaced along said long axis, the indicia correlating to a position of said indicia along said long axis, and a sensor secured to said housing, said sensor including:

means to read said indicia adjacent said sensor, means to correlate said indicia adjacent said sensor with a position of said plunger along said plunger axis, and means to display plunger position information from said correlating means in visually perceptible form.

11. The system of claim 10 wherein said correlating means includes means to be selectively zeroed such that linear displacement of the plunger away from a location at which the correlating means was zeroed, can be quantified.

12. The system of claim 11 wherein said means to secure said slide to said plunger includes a collet, said collet including means to adjust a diameter thereof to selectively grasp and release a button at an end of the plunger of the syringe.

13. The system of claim 12 wherein said slide is supported along a linear pathway adjacent said housing with a linear bearing, said linear bearing preventing said slide from moving non-parallel to said plunger axis.

14. The system of claim 13 wherein an adjustable braking mechanism is oriented between said housing and said slide, said adjustable braking mechanism including means to adjust a friction force experienced by said slide when said slide is translated linearly with respect to said housing.

15. The system of claim 10 further including an adjustable stop including means to limit linear translation of said slide along said long axis of said slide beyond said stop.

16. The system of claim 10 wherein said display means includes means to concurrently display plunger position information as said information is received from said correlating means.

17. The system of claim 10 wherein said means to secure said slide to said plunger includes a collet, said collet including means to adjust a diameter thereof to selectively grasp and release a button at an end of the plunger of the syringe.

18. The system of claim 10 wherein said slide is supported along a linear pathway adjacent said housing with a linear bearing, said linear bearing preventing said slide from moving non-parallel to said plunger axis.

19. The system of claim 10 wherein an adjustable braking mechanism is oriented between said housing and said slide, said adjustable braking mechanism including means to adjust a friction force experienced by said slide when said slide is translated linearly with respect to said housing.

20. A method for dispensing precise quantities of liquid from a syringe which has a plunger that reciprocates linearly in a syringe body, the steps including:

fixing the syringe body to a dispensing indicator housing, attaching a sensor on the dispenser indicator housing, attaching the syringe plunger to a dispensing indicator plunger, constraining the plungers to move linearly, parallel and in synchrony, orienting the dispensing indicator plunger to pass by the sensor on the dispenser indicator housing, sensing the dispensing indicator plunger's linear movement, displaying the linear movement on a visually readable output.

21. A releasably attachable manual dispensing aid operable with a syringe having a syringe body and a syringe plunger slidable within the syringe body, the dispensing aid comprising:

a dispensing aid body;

a slide that is slidable within the dispensing aid body;

means for releasably attaching the dispensing aid body directly to the syringe body;

a dispensing aid plunger connected to the slide, the dispensing aid plunger being directly graspable and operable by a human hand to produce a linear motion of the slide;

means for releasably attaching the dispensing aid plunger to the syringe plunger; and an electronic linear position measuring device having a first portion fixed to the dispensing aid body and a second portion fixed to the dispensing aid plunger;

wherein the electronic linear position measuring device relies on capacitance means and produces an output responsive to capacitance between the first portion and the second portion.

22. The dispensing aid of claim 21, further including a digital readout whose output signal is responsive to a readout signal from the linear position measuring device.

23. The dispensing aid of claim 21, further including a microprocessor which receives an output signal from the linear position measuring device.

24. A releasably attachable manual dispensing aid operable with a syringe having a syringe body and a syringe plunger slidable within the syringe body, the dispensing aid comprising:

a dispensing aid body;

a slide that is slidable within the dispensing aid body;

means for releasably attaching the dispensing aid body directly to the syringe body;

a dispensing aid plunger connected to the slide, the dispensing aid plunger being directly graspable and operable by a human hand to produce a linear motion of the slide;

means for releasably attaching the dispensing aid plunger to the syringe plunger;

an electronic linear position measuring device having a first portion fixed to the dispensing aid body and a second portion fixed to the dispensing aid plunger; and an adjustable stop that limits the linear movement of the dispensing aid plunger relative to the dispensing aid body.

25. The dispensing aid of claim 24 including a digital readout whose output signal is responsive to a readout signal from the linear position measuring device.

26. The dispensing aid of claim 24 further including a microprocessor which receives an output signal from the linear position measuring device.

27. A releasably attachable manual dispensing aid operable with a syringe having a syringe body and a syringe plunger slidable within the syringe body, the dispensing aid comprising:

a dispensing aid body;

a slide that is slidable within the dispensing aid body;

means for releasably attaching the dispensing aid body directly to the syringe body;

a dispensing aid plunger connected to the slide, the dispensing aid plunger being directly graspable and operable by a human hand to produce a linear motion of the slide;

means for releasably attaching the dispensing aid plunger to the syringe plunger;

an electronic linear position measuring device having a first portion fixed to the dispensing aid body and a second portion fixed to the dispensing aid plunger; and a drag brake pad selectively engagable with the slide to apply a drag braking force to the movement of the slide.

28. The dispensing aid of claim 27 including a digital readout whose output signal is responsive to a readout signal from the linear position measuring device.

29. The dispensing aid of claim 27 further including a microprocessor which receives an output signal from the linear position measuring device.

30. A releasably attachable manual dispensing aid operable with a syringe having a syringe body and a syringe plunger slidable within the syringe body, the dispensing aid comprising:

a dispensing aid body;

a slide that is slidable within the dispensing aid body;

means for releasably attaching the dispensing aid body directly to the syringe body;

a dispensing aid plunger directly graspable and operable by a human hand to produce a linear motion of the slide;

means for releasably attaching the dispensing aid plunger to the syringe plunger;

an electronic linear position measuring device comprising a first portion fixed to the dispensing aid body and having a first metallic electrode, a second portion fixed to the dispensing aid plunger and having a second metallic electrode disposed in a facing relation to the first metallic electrode, and means for measuring a capacitance of a circuit including the first metallic electrode and the second metallic electrode and producing an output linear position signal responsive to the measured capacitance;

a microprocessor which receives the output linear position signal of the means for measuring and produces a microprocessor output signal;

a readout which receives the microprocessor output signal; and an adjustable stop that limits the linear movement of the dispensing aid plunger relative to the dispensing aid body.

31. A releasably attachable manual dispensing aid operable with a syringe having a syringe body and a syringe plunger slidable within the syringe body, the dispensing aid comprising:

a dispensing aid body;

a slide that is slidable within the dispensing aid body;

means for releasably attaching the dispensing aid body directly to the syringe body;

a dispensing aid plunger directly graspable and operable by a human hand to produce a linear motion of the slide;

means for releasably attaching the dispensing aid plunger to the syringe plunger;

an electronic linear position measuring device comprising a first portion fixed to the dispensing aid body and having a first metallic electrode, a second portion fixed to the dispensing aid plunger and having a second metallic electrode disposed in a facing relation to the first metallic electrode, and means for measuring a capacitance of a circuit including the first metallic electrode and the second metallic electrode and producing an output linear position signal responsive to the measured capacitance;

a microprocessor which receives the output linear position signal of the means for measuring and produces a microprocessor output signal; and a readout which receives the microprocessor output signal;

wherein the means for releasably attaching the dispensing aid body to the syringe body includes a clip.

32. A releasably attachable manual dispensing aid operable with a syringe having a syringe body and a syringe plunger slidable within the syringe body, the dispensing aid comprising:

a dispensing aid body;

a slide that is slidable within the dispensing aid body;

means for releasably attaching the dispensing aid body directly to the syringe body;

a dispensing aid plunger directly graspable and operable by a human hand to produce a linear motion of the slide;

means for releasably attaching the dispensing aid plunger to the syringe plunger;

an electronic linear position measuring device comprising a first portion fixed to the dispensing aid body and having a first metallic electrode, a second portion fixed to the dispensing aid plunger and having a second metallic electrode disposed in a facing relation to the first metallic electrode, and means for measuring a capacitance of a circuit including the first metallic electrode and the second metallic electrode and producing an output linear position signal responsive to the measured capacitance;

a microprocessor which receives the output linear position signal of the means for measuring and produces a microprocessor output signal; and a readout which receives the microprocessor output signal;

wherein said means for attaching the dispensing aid plunger to the syringe plunger includes means to move a plunger clip from a first open position to a second retained position on the plunger.

33. A releasably attachable manual dispensing aid operable with a syringe having a syringe body and a syringe plunger slidable within the syringe body, the dispensing aid comprising:

a dispensing aid body;

a slide that is slidable within the dispensing aid body;

means for releasably attaching the dispensing aid body directly to the syringe body;

a dispensing aid plunger directly graspable and operable by a human hand to produce a linear motion of the slide;

means for releasably attaching the dispensing aid plunger to the syringe plunger;

an electronic linear position measuring device comprising a first portion fixed to the dispensing aid body and having a first metallic electrode, a second portion fixed to the dispensing aid plunger and having a second metallic electrode disposed in a facing relation to the first metallic electrode, and means for measuring a capacitance of a circuit including the first metallic electrode and the second metallic electrode and producing an output linear position signal responsive to the measured capacitance;

a microprocessor which receives the output linear position signal of the means for measuring and produces a microprocessor output signal;

a readout which receives the microprocessor output signal; and an output plug for the microprocessor output signal.

34. A dispensing aid for a syringe having a long axis and having a body carrying fluid in a bore coincident with the long axis, the syringe including a plunger which reciprocates in the bore, the dispensing aid comprising, in combination:

a housing, means for holding the syringe body to the housing, a first indicator operatively coupled to said housing, means for removably fastening the syringe plunger to said first indicator such that said first indicator and the plunger move in synchrony and parallel to said long axis, a second indicator fixed on said housing, means for moving said first indicator with respect to said second indicator, and means for determining and displaying the positional relationship between said first and second indicators;

wherein said means for holding the body to the housing includes a recess formed in the housing, said recess sized to support an enlargement on the body of the syringe in a manner restraining linear displacement of the syringe parallel to the long axis, and wherein said housing includes a clip adapted to secure said enlargement from translation non-parallel to the housing, whereby the body of the syringe is held securely to said housing.

35. The dispensing aid of claim 34 wherein said first indicator and said second indicator include means to detect a distance therebetween in a direction parallel to the long axis, such that a relative position of the plunger within the body, corresponding to the distance between said first indicator and said second indicator can be established.

36. A dispensing aid for a syringe having a long axis and having a body carrying fluid in a bore coincident with the long axis, the syringe including a plunger which reciprocates in the bore, the dispensing aid comprising, in combination:

a housing, means for holding the syringe body to the housing, a first indicator operatively coupled to said housing, means for removably fastening the syringe plunger to said first indicator such that said first indicator and the plunger move in synchrony and parallel to said long axis, a second indicator fixed on said housing, means for moving said first indicator with respect to said second indicator, and means for determining and displaying the positional relationship between said first and second indicators;

wherein said means for removably fastening the plunger to said first indicator includes a collet fastener and means to selectively expand and contract a diameter of the collet fastener to grasp and release a button on an end of the plunger.

37. The dispensing aid of claim 36 wherein said first indicator and said second indicator include means to detect a distance therebetween in a direction parallel to the long axis, such that a relative position of the plunger within the body, corresponding to the distance between said first indicator and said second indicator can be established.

38. A dispensing aid for a syringe having a long axis and having a body carrying fluid in a bore coincident with the long axis, the syringe including a plunger which reciprocates in the bore, the dispensing aid comprising, in combination:

a housing, means for holding the syringe body to the housing, a first indicator operatively coupled to said housing, means for removably fastening the syringe plunger to said first indicator such that said first indicator and the plunger move in synchrony and parallel to said long axis, a second indicator fixed on said housing, means for moving said first indicator with respect to said second indicator, and means for determining and displaying the positional relationship between said first and second indicators;

wherein said first indicator includes an elongate slide oriented with a long axis thereof parallel to the long axis of the syringe, said slide including means to coact with said second indicator to determine a relative distance between said first indicator and said second indicator.

39. The dispensing aid of claim 38 wherein said first indicator and said second indicator include means to detect a distance therebetween in a direction parallel to the long axis, such that a relative position of the plunger within the body, corresponding to the distance between said first indicator and said second indicator can be established.

40. The dispensing aid of claim 38 wherein said slide includes a bearing support restricting slide motion to a line parallel to the long axis of the syringe.

41. The dispensing aid of claim 40 wherein an adjustable friction brake is oriented between said housing and said slide, said adjustable friction brake including means to adjust friction forces experienced by said slide as said slide moves parallel to the long axis of the syringe, whereby an ease of motion of the slide and the plunger can be adjusted.

* * * * *

UNITED STATES PATENT AND TRADEMARK OFFICE
CERTIFICATE OF CORRECTION

PATENT NO. : 5,611,784
DATED : March 18, 1997
INVENTOR(S) : Barresi, et al.

It is certified that error appears in the above-indentified patent and that said Letters Patent is hereby corrected as shown below:

In the drawing sheet 7, Figure 10, Kindly change "valve" to --value-- in the block referenced by numeral 94.

Signed and Sealed this

Twenty-third Day of September, 1997

Attest:

BRUCE LEHMAN

Attesting Officer

Commissioner of Patents and Trademarks